United States Patent [19]

Alekhin et al.

[11] 4,370,885

[45] Feb. 1, 1983

[54] METHOD FOR CONTROLLING THE DISPERSING OF SOLIDS IN DRILLING MUD

[76] Inventors: Stanislav A. Alekhin, Chilanzar, kvartal 24, 53, kv. 89; Vitold M. Bakhir, proezd Gaidara, 7-A, kv. 17; Raisa I. Born, Chilanzar, kvartal 24, 53, kv. 89; Tatyana M. Bakhir, proezd Gaidara, 7-A, kv. 17, all of Tashkent, U.S.S.R.

[21] Appl. No.: 197,101

[22] PCT Filed: Dec. 29, 1979

[86] PCT No.: PCT/SU79/00137

§ 371 Date: Sep. 16, 1980

§ 102(e) Date: Sep. 15, 1980

[87] PCT Pub. No.: WO80/01496

PCT Pub. Date: Jul. 24, 1980

[30] Foreign Application Priority Data

Jan. 16, 1979 [SU] U.S.S.R. .............................. 2705513

[51] Int. Cl.³ .............................................. E21B 47/00
[52] U.S. Cl. ......................................... 73/153; 175/40
[58] Field of Search ...................... 73/153, 61.4, 64.1; 324/71 CP; 175/40

[56] References Cited

U.S. PATENT DOCUMENTS

4,178,796 12/1979 Zwicker et al. ................... 73/61.4

FOREIGN PATENT DOCUMENTS

930943 10/1976 U.S.S.R. .

*Primary Examiner*—Jerry W. Myracle
*Attorney, Agent, or Firm*—Fleit & Jacobson

[57] ABSTRACT

A method for controlling the dispersing of solids in drilling mud, consisting in that mud mineralization value is measured continuously until it stabilizes itself in the course of the dispersing, the variation of the mud mineralization value being used to determine the concentration of particles of the drilling mud solid phase.

4 Claims, 2 Drawing Figures

METHOD FOR CONTROLLING THE DISPERSING OF SOLIDS IN DRILLING MUD

BACKGROUND ART

The present invention relates to the preparation of drilling muds, pulps and suspensions, and, in particular to methods for controlling the dispersing of solids in drilling muds.

The present invention can be used to good advantage in the petroleum and gas industries for preparing drilling muds.

The dispersing of solids is a critical process operation, as it governs to a great degree the quality of the prepared drilling mud. An effective dispersing of clays reduces their consumption through greater yield of drilling mud per unit mass of clay powder. A reduction in the total amount of solids in the mud while retaining the colloidal state factor value raises the penetration rate.

Dispersing is employed for preparing drilling muds based on clay materials, wherever the clay powders possess a low colloidal state factor.

The dispersing of solids in a liquid phase involves physicochemical changes affecting the state and the properties of both the solid and the liquid phases. A measure of the dispersing effectiveness is the fineness of the solid phase, described in terms of the concentration of particle thereof in the mud.

It is common knowledge that the most active clay particles as regards the drilling mud structure formation are ones measuring 5 $\mu$m and less across. The dispersing consists in converting a maximum possible proportion of the solid phase to colloidal particles less than 5 $\mu$m across.

However, of major importance in the formation of the coagulation structure is not only the size of the colloidal particles, but also their number, i.e. the concentration of particles. In practice, a small number of solid colloid particles fails to ensure a strong coagulation structure, whereas their excess number may sharply increase the gel strength and the flow resistance of the mud and so bring down the penetration rate and hamper the removal of cuttings from the drilling mud. The optimum concentration of particles of the solid phase in a drilling mud varies with the type thereof, so that the concentration of particles is one of the main parameters characterizing the drilling mud solid phase dispersion.

There is known a method for monitoring the dispersing of solids in drilling mud by measuring the electric parameters thereof. The method consists essentially in placing electrodes in a liquid stream and measuring the difference of potentials across electrodes, as particles move together with the stream and with respect to the liquid.

This phenomenon, termed the electrokinetic effect, is due to a double electric layer at the solid-particle-liquid interface, as the solid particle and the liquid possess a definite charge. The electrokinetic potential in the drilling mud stream varies with the change in the concentration of the solid phase particles. The greater the concentration of particles in the liquid, the greater is the electrokinetic potential, as the difference in the potentials is governed by the charge transmitted by the particles to the electrodes of the measuring apparatus. The greater the number of these particles, the greater is the potential difference.

Therefore, the determination of the electric parameters of a drilling mud, in particular, of the electrokinetic potential thereof, provides information on the solid phase fineness, which is taken to indicate the degree of dispersion.

The prior art method makes it possible to control the variation of the amount of the solid phase in the liquid, but fails to ensure a continuous control of the dispersing of solids in drilling mud and to determine the end of the solid phase dispersion, this providing no means for preparing the drilling mud under optimum conditions. In addition, the method necessitates a system of electrodes with recorders, their erection, setting-up and servicing, this involving extra labour and power consumption.

There is also known a method for controlling the dispersing of solids in drilling, wherein the concentration of solids is measured by means of a vibration-type pickup consisting of an oscillation exciter formed with a mechanical oscillation converter and a detecting element having a grid frame, the plane of which is perpendicular to the direction of oscillations. The grid frame of the vibration pickup is rigidly connected to the oscillation exciter and is immersed into the drilling mud stream at the right angle to its flow. If solid phase particles in the mud are larger than the clear openings in the grid frame, they block the apertures of the grid, thereby sharply increasing the resistance the detecting element offers to flow. The greater the concentration of solid phase particles in the mud, the greater is the resistance to flow of the grid, this reducing the detecting element oscillation amplitude, the magnitude of which is a measure of the concentration of solids in the liquid phase. The greater the concentration of particles in the mud, the higher is the degree of dispersion.

Therefore, the variation of the amplitude of oscillations of the detecting elements indicates the variation in the concentration of particles in the liquid phase. However, this known method also fails to provide a continuous control of the dispersing of solids in drilling mud and the determination of the optimum solid phase dispering time, particularly where the solid phase is clays of various mineralogical compositions having different starting strengths of clay particles. The various types of clays present different colloidal state factors with the effect that the specified size of the particles being dispersed has different values. Therefore, the application of this known method requires to change the detecting element with each type of clay, a suitably apertured frame being selected each time. This results in a periodic discontinuance of the dispersing process and the re-setting of the dispersing apparatus operating parameters, leads to additional consumptions of labor and power and lowers the throughput capacity of the dispersing apparatus. Dispersing under non-optimum conditions would bring about either an over-dispersion of the solid phase in the liquid phase with attendant excess power consumption or insufficient dispersion of large and tough particles with, in both cases, resultant instability and deterioration of drilling mud properties.

DISCLOSURE OF THE INVENTION

The invention has as its aim the provision of a method for controlling the dispersing of solids in drilling mud, which would make it possible to control continuously the dispersing process by measuring continuously one of the parameters characterizing mud properties.

According to the invention, there is provided a method for controlling the dispersing of solids in drilling mud, consisting in measuring the concentration of particles, wherein the concentration of particles is determined on the variation of mud mineralization measured continuously in the course of dispersing until the mineralization stabilizes itself, the increase in mud mineralization being used to evaluate that of the concentration of solids and the stabilization of mud mineralization being taken to indicate the maximum concentration of particles.

This provides a means to achive an optimum dispersion of the solid phase through determination of the optimum dispersing time.

In the final analysis, these refinements substantially reduce power consumption and improve drilling mud properties through optimum dispersing conditions and effective breaking up of solids to colloidal size.

BRIEF DESCRIPTION OF DRAWINGS

The invention will now be described, by way of example, with reference to the accompanying drawings, in which.

BEST MODE OF CARRYING OUT THE INVENTION

It is well known that clays contain potassium, calcium, sodium ions which partly dissolve in water, so increasing the degree of mineralization of drilling mud. For example, montmorillonite and hydromica clays have the following chemical composition, %:
$SiO_2$, 41.6–76; $Al_2O_3$, 6.86–25.88; FeO, 0.19–4.9;
MgO, 0.22–0.26; CaO, 0.9–14.3; MnO, 0.03–0.04;
TiO, 0.2–1.4; $P_2O_3$, 0.15–5.17; $Na_2O$, 0.38–2.85
$K_2O$, 0.18–7.5; $CO_2$, 0.26–2.15; $Fe_2O_3$, 2.0–14.61.

The chemical composition indicates that clays contain a fair proportion of alkali-earth elements.

In case of vigorous dispersing action upon the solid phase, coarse solids are broken up into fine particles to expose new surfaces at fractures, so that more alkali-earth elements dissolve in water to raise the degree of mineralization of the drilling mud. Therefore, the greater is the fineness of clay particles, the greater the concentration of particles and the higher the degree of mineralization of the drilling mud.

Figure 1:
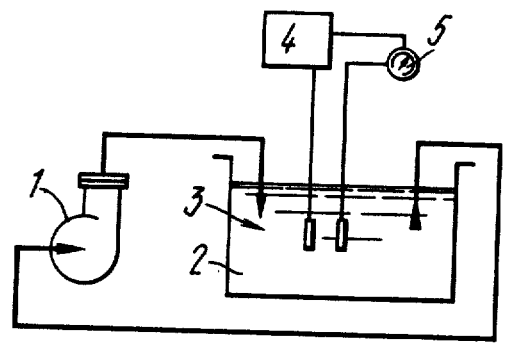
FIG. 1 illustrates a schematic embodiment of a method, according to the invention.

Usually, a water-and-clay suspension is processed in a disperser 1 (FIG. 1), for example, of a widely known rotor-pulse type consisting essentially of a rotor and a stator (not shown on the figure) of cylindrical shapes provided with notches and projections and located coaxially inside a housing. In such a disperser, solids are broken up through cavitation phenomena in a pulsing stream of liquid passing through the stator notches which are shut off at regular intervals of time by the rotor projections. Dispersing is continued until the greater part of the solids is converted to colloidal state, that is broken up to particles less than 5 μm across.

However, various types of clays possess different toughnesses with the effect that, all other conditions being equal (disperser throughput capacity, volume concentration of solids in the drilling mud, intensity of dispersing action), the optimization of the dispersing conditions depends on the time during which the pulp is processed. At the same time, a lack of suitable means makes it impossible to control continuously the variation in the concentration of particles in the course of dispersing and so to determine the optimum dispersing time for various types of clays.

To provide such a means for determining the optimum dispersing time, a receiving tank 2 is fitted with a pickup 3 for controlling the drilling mud mineralization, the pickup being connected to an electric power supply source 4 and a recorder 5.

The pickup 3 for controlling the mineralization of the drilling mud may be any of the widely known apparatus for measuring the electric conductivity of electrolytes, which consist of two electrodes immersed in an electro-conductive liquid and connected to the electric power supply source and to the recorder. The greater the amount of mineral components dissolved in the liquid phase of the mud during the dispersing of the solids in the liquid phase, the lower is the electric resistance of the liquid phase and the greater will be the electric current between the electrodes, the magnitude of which will be put down on the diagram of the recorder 5. Therefore, the more intensive the dispersing of the solids in the liquid phase, the higher is the mineralization of the liquid phase, or the lesser the electric resistance of the liquid phase and, accordingly, the higher the intensity of the electric current between the electrodes, the variation of the electric current between the electrodes indicating the variation of the degree of dispersion of the solid phase.

The mineralization of the drilling mud, which varies with the fineness of the solid phase, can be monitored by other methods as well.

Figure 2:
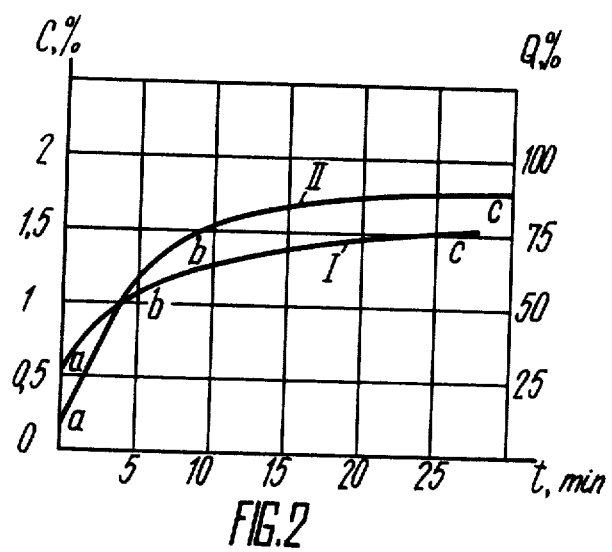
FIG. 2 presents a curve (I) illustrating the variation of the degree of mineralization of a drilling mud prepared with 20 weight percent of clay powder and a curve (II) illustrating the variation of the concentration of particles.

FIG. 2 illustrates the curve (I) of the variation of the mineralization (C%) of a drilling mud, prepared from clay powder 20% by volume and water, as a function of the dispersing time and the curve (II) of the concentration of particles (G %) as a function of the dispersing time.

As the curves of the FIG. 2 indicate, the mineralization of the mud (and with it, the concentration of particles) rises sharply during roughly the initial 20 minutes of the dispersing, after which the curve eases to a slight slope, this indicating that the dispersing has passed the optimum point. Therefore, the concentration of particles in the drilling mud can be determined from the mineralization value which is measured continuously in the course of dispersing, the increase in the mineralization value (length ab) indicating that of the concentration of particles, and the steadying of the mineralization value (length bc), the maximum concentration of particles.

The greater the concentration of particles in a drilling mud, the higher is the degree of dispersion of the drilling mud.

The method according to the invention for controlling the dispersing of solids in drilling mud provides a continuous reading on the dispersing of the drilling mud, and with it a means for determining optimum dispersing time and for considerably lowering power consumption.

The method is easy to carry out and substantially improves drilling mud properties through more accurate control of one of the parameters, specifically the concentration of particles, other advantages including considerably lesser consumptions of power, materials and time for preparing the drilling mud, as the process is discontinued in good time on readings of the mud mineralization pickup.

The effect of all this is:

a reduction in the consumption of solid materials of 10 to 15%;

an increase in the throughput capacity of the dispersing equipment of 15 to 20%;

a drop in power consumption of 20 to 25%;

a decrease in the dispersing time of 10 to 15%.

What is claimed is:

1. A method for controlling the dispersing of solids in drilling mud by measuring the concentration of particles, comprising determining the concentration of particles of the solid phase by continuously measuring the variation of the mud mineralization during the course of dispersing until a point is reached at which the mineralization value is stabilized, an increase in the mineralization value indicating an increase in the concentration of particles of the solid phase, and the stabilizing of the mineralization value indicating the maximum value of the concentration of particles of the solid phase, and discontinuing the dispersing of solids when said mineralization value is substantially stabilized.

2. The method of claim 1, wherein the dispersing of solids is continued until the stabilization of the mineralization value indicates a particle size of the solid phase of less than 5 $\mu$m in diameter.

3. The method of claim 1, wherein the mineralization value is continuously measured by measuring the electric conductivity using two electrodes in the liquid phase.

4. The method of claim 3, wherein the variation in the electric conductivity is recorded.